(12) United States Patent
Zaaijer et al.

(10) Patent No.: US 11,978,531 B2
(45) Date of Patent: May 7, 2024

(54) METHOD FOR MONITORING AND MANAGEMENT OF CELL LINES USING PERIODIC LOW-COVERAGE DNA SEQUENCING DATA

(71) Applicant: The Joan and Irwin Jacobs Technion-Cornell Institute, New York, NY (US)

(72) Inventors: Sophie Zaaijer, New York, NY (US); Tyler Joseph, New York, NY (US)

(73) Assignee: The Joan and Irwin Jacobs Technion-Cornell Institute, New York, NY (US)

( * ) Notice: Subject to any disclaimer, the term of this patent is extended or adjusted under 35 U.S.C. 154(b) by 743 days.

(21) Appl. No.: 16/740,327

(22) Filed: Jan. 10, 2020

(65) Prior Publication Data
US 2021/0217486 A1 Jul. 15, 2021

(51) Int. Cl.
*G06F 16/00* (2019.01)
*G16B 10/00* (2019.01)
*G16B 20/20* (2019.01)
*G16B 30/00* (2019.01)

(52) U.S. Cl.
CPC .............. *G16B 10/00* (2019.02); *G16B 20/20* (2019.02); *G16B 30/00* (2019.02)

(58) Field of Classification Search
None
See application file for complete search history.

(56) References Cited

U.S. PATENT DOCUMENTS

| | | |
|---|---|---|
| 2011/0269154 A1 | 11/2011 | Fantl et al. |
| 2019/0256924 A1 | 8/2019 | Vogelstein et al. |
| 2020/0167914 A1* | 5/2020 | Stamatoyannopoulos ................. G16B 40/20 |

FOREIGN PATENT DOCUMENTS

WO WO-2019113499 A1 * 6/2019 ......... C12N 15/1079

OTHER PUBLICATIONS

International Search Report and Written Opinion dated Mar. 19, 2021, for International Application No. PCT/US2020/065084, 7 pages.
Ben-David, U., et al., "Genetic and transcriptional evolution alters cancer cell line drug response", Nature. Aug. 2018; 560(7718): 325-330.
Zaaijer, S., et al., "Tracking cell lineages to improve research reproducibility", Nat Biotechnol. May 19, 2021; 6(39): 666-670.
Selznick et al., "Development and application of computer software for cell culture laboratory management." In Vitro Cellular & Developmental Biology-Animal. Jan. 2001; 37: 55-61.
Viader-Llargues et al., "Live cell-lineage tracing and machine learning reveal patterns of organ regeneration." eLIFE. Mar. 29, 2018; 7:e30823. 23 pages.

* cited by examiner

*Primary Examiner* — Tuankhanh D Phan
(74) *Attorney, Agent, or Firm* — Cooley LLP

(57) ABSTRACT

A method and system are provided for tracking and verifying cell populations that constitute a given cell lineage. By tracking the creation of cell populations along the cell lineage as a directed tree, it is possible to verify multiple cell populations using a single cell population. Similarly it is possible to detect potentially anomalous cell populations by performing a verification determination on a single cell population.

20 Claims, 14 Drawing Sheets

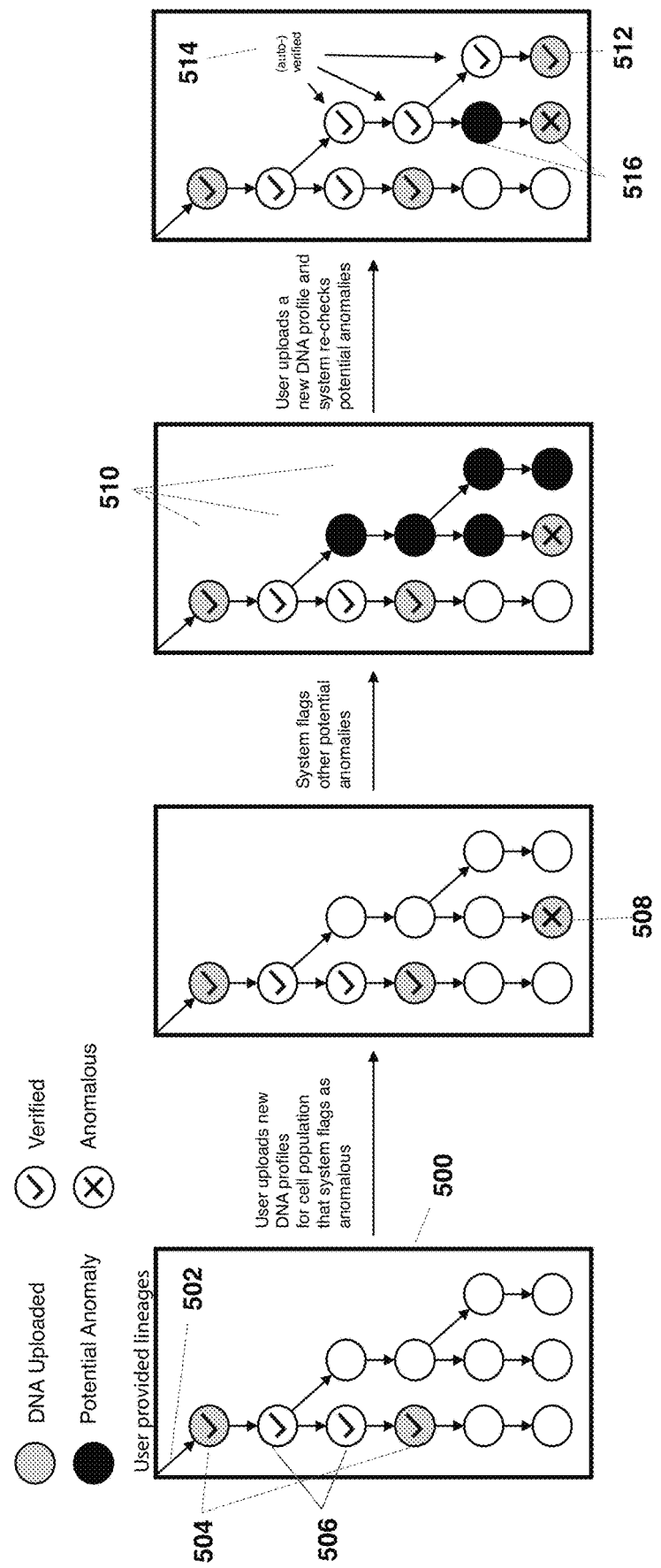

METHOD FOR MONITORING AND MANAGEMENT OF CELL LINES USING PERIODIC LOW-COVERAGE DNA SEQUENCING DATA

BACKGROUND

Cell lines form the cornerstone of a biomedical market, worth billions of dollars. In vitro-grown human cells derived from patient tissues are critical in biomedical research such as drug discovery and production, regenerative medicine, treatment of disease. Cell lines also play a vital role in the identification of personalized drug treatments for individual patients (referred to as "precision medicine").

Cell lines are established when i) in vivo cells are taken from a human body and placed in a petri dish (in vitro), and ii) they able to proliferate over long periods of time. The moment they are placed in a petri dish, cells must be "passaged" to prevent running out of nutrients and space. The passaging process is an error-prone process that is labor intensive and cumbersome to track.

The oldest human cell line was established in 1951. Derived from then 31-year-old Henrietta Lacks, referred to as HeLa cells. These have been proliferating in vitro for nearly 70 years. HeLa's many cell lineages are widely used in biomedical laboratories and are shipped to biomedical researchers in thousands of laboratories all over the world. This cell line alone, has helped millions of patients around the globe, aiding the development of new drugs and medical treatments.

Problem Statement & Background

Lineage Tracking and Verification

Over the years the HeLa cell line has been used in experiments described in roughly 100,000 publications. Distribution of the cell line has occurred through lab-to-lab sharing, or via lab purchases from biobanks that maintain stocks of HeLa cells. Examples of centralized 'biobanks' are the ATCC, or the Coriell Institute. Each time a cell population is split and shared, this creates a new "cell lineage": a new branch in the history of the cell line that follows its own in vitro evolutionary path. There is a distinction between cell strain and cell lineage. Cell strains are cells derived from the initial patient cell lines that were then introduced with a new characteristic (e.g. mutation, transgenic construct). Within a cell strain you can again have separate cell lineages if the cell strain is split and grown in two separate petri-dishes. Here we refer to "cell lineages" as they are most specific.

The "pedigree" or "lineage tree," of cell line exchanges has not been recorded systematically. The number of independent passages, the time between passages, and the duration of cell lineage storage in freezers are mostly unknown. This information is critical to prevent the propagation of invalid cell lines throughout the scientific community. Examples of such invalid cell lines include, errors in unstable cell lines (such as HeLa), cell lines that acquired a genetic aberrancy (e.g., stem cells), or invasive contamination events.

Knowledge of the cell line lineage tree is also critical because the process of passaging and sharing cell lines is subject to human error. Indeed, mislabeling, cell line contamination, and subsequent sharing has resulted that 20% of the current cell populations is incorrect. These are circulating in the biomedical field. Lack of routine DNA verification is a crucial factor in the spread of errors and irreproducible results in the community of users. This process bears analogy to the game of "telephone," in that it is characterized by a propagating chain of errors that are passed on to multiple parties. In the case of cell lines, error propagation is not limited to a linear chain of individuals, and errors may multiply undetected through a network of laboratories and individual scientists. Error sources include:

1. Mislabeling: Laboratory workers often handle many cell populations at once, and these are not easily discriminated by eye or microscope and cell lines risk being mislabeled. In addition, the lab worker requires recording and logging the information, which is labor intensive, time consuming and potentially error prone.
2. Cell line contamination: Contamination by other cell lines is a major issue. Contamination is suspected to occur when cell lines are transferred via contaminated media, pipette tips, or other techniques. It only takes a single cell with a shorter cell cycle to overgrow and replace the other cell line in a matter of days.

The International Committee for Cell Line Authentication (ICLAC) has done extensive work to identify incorrect cell lines, such as cell lines that have been mislabeled or contaminated. ICLAC has frequently observed occasions where HeLa cells, or other cell lines, have replaced the cell line of interest, which poses a true risk for the reproducibility of scientific work.

Financial Impact of the Problem:

The lack of systematic management solutions is a major cause of irreproducible research. According to a PLOS Biology publication in 2015 by Freedman et al, entitled: "The Economics of Reproducibility in Preclinical Research"—it leads to a waste of $9 billion dollars annually in the USA alone. The translation of the problem in financial loss is best illustrated when looking into drug discovery. Drug discovery research is done through testing the efficacy of candidate drugs on human cell lines. Using an incorrect cell line at this stage could result in a false negative lead, where a drug fails that would otherwise be successful, or conversely false positive leads. The latter subsequently triggers follow up experiments, and investment in time, reagents and labor.

An average drug costs ~3 Billion USD to push from drug discovery to FDA approval, and takes roughly 13 years. This process is split up into pre-clinical drug discovery and clinical trials. The drugs that pass all pre-clinical validations are passed to phase I clinical trails. However, only 30% drug candidates are successful in phase I. This can be for various reasons such as translating from cell culture to multicellular system, or from mouse model to human model. But the fact that 20% are incorrect as described above also contributes to the inability to translate the findings from in vitro to in vivo state. It is important to minimize the risk of false positives or negatives in these early stages of testing, since screening thousands of compounds for finding candidate drugs is expensive. Furthermore, since phase I clinical trials are costly, it is critical to not let false positive candidate drugs transition from the pre-clinical phase. Genetically monitoring cell lines to ensure they are correct would be a cost-effective step to make the process of drug discovery more efficient as it would minimize both false negatives and positives.

State of the Art Laboratory Management Systems:

Laboratory workers currently have a limited set of tools available to assess the veracity of their cell lines. Routine quality control for cell lines is currently done by three independent functioning tools: 1) DNA analysis, 2) LIMS, 3) Protocol management.

The most commonly used technique for cell identification is adopted from the forensics community: profiling short-tandem repeats (STRs, a type of variable genetic marker) using capillary electrophoresis. The profiled STRs are compared against databases of cell line's STR profiles (e.g. the ATCC STR database, DSMZ, Broad Institute Cancer Cell Line Encyclopedia, or ExPASy databases). Cellosaurus a public cell line catalogue provides genetic (STR) profiles for common cell lines. However, utilization of these databases for verification requires in-house bioinformatics tools and know how. Typically, services from DNA service labs are used, including ATCC, LabCorp, Charles River. The PDF reports about the cell line (not population) provided by the DNA service lab may be linked to a lab notebook entry, either in printed form or electronically. In addition to STR panels, increasingly SNP panels are adopted (which profile a specific set of genome wide genetic variant loci, frequently 50-80 SNPs). Other standard genetic tests include genetic stability testing using karyotypes or CGH array.

Laboratories seeking transparency on the whereabout of their physical reagents in the laboratory over time (including cell lines, enzymes, chemicals, DNA samples) use a laboratory information management system (LIMS), such as one that is provided by various companies. These software systems enable tracking of tubes with biospecimen. LIMS systems are specialized in integrating metadata about the biospecimen (black and white barcode, labeling system), to track the positions of tubes. This includes position in the freezer, fridge or, in which laboratory they are.

Tracking protocols, logging actions and observations by laboratory workers is tracked in laboratory notebooks. Notebooks include notes on specifics in the process of passaging, such as how many cells are transferred from one petri-dish to the other, and what media they used. Most laboratory protocols involving manipulations to cell lines are very long and cumbersome. For instance, the generation of induced pluripotent stem cells takes weeks/months. The entries into notebooks will be spread out over weeks and buried into other experiments and notes. The notebooks can be paper, but are increasingly digital.

Nonetheless, both genetic and management solutions above come with limitations. For example, LIMS does not have integration with high accuracy biological verification, nor does it verify user-filled relationships between the living entity in the tube. Also, except for flipping back through your notebook pages, you cannot compare activities easily in one go—to pick up modifications of work protocols, reagents used, or individuals who are executing the protocols, and the biological consequences. Also, collaboration using this method requires pre-agreed upon nomenclature and note-taking, which is often not the case. Lastly, STR profiles only catalog a small fraction of the variation in an individual's genome, and thus provide limited utility in detecting genomic contamination. Only common cell lines have STR profiles available, no such catalog exists for a cell line developed within a lab. Moreover, cell line verification services require sending cell populations to an external lab. It can take weeks to return results.

Perhaps most importantly, the current single genetics tests do not consider the sequential continuous nature of a living cell line, consisting of cell lineages, and individual cell populations. The lack of a cell line lineage tree map limits the ability to assess how a cell population that fails verification impacts other lineages (i.e., descendants) in the lab. The latter point is critical to solve the long-standing problem of cell line authentication and cell line tracking in the network of scientific endeavors by academia, pharmaceutical industry and other stakeholders.

The widespread availability and reduced cost of next generation sequencing technology that is getting faster, real-time and more portable, is an opportunity to address these challenges.

SUMMARY OF THE INVENTION

A method for monitoring and management of cell lines using periodic low-coverage DNA sequencing is described. The method comprises three components creating a significant improvement over the state-of-the-art methods for in vitro cell tissue management. The first component is a method for genetic verification of cell lines from low-coverage DNA sequencing of an in vitro cell population. Genetic profiles of cell lines are stored in a database. Low-coverage DNA sequencing is performed on a cell population, and the resulting DNA sequencing reads are compared to the database of genetic profiles to determine the genetic identity of the cell population and detect contamination. The second component is a computer system that stores cell line lineages as a directed tree (a type of directed acyclic graph), along with genetic profiles of cell populations generated by low-coverage DNA sequencing. The system incorporates the biology of a proliferating cell line by subdividing a cell line lineage into "cell populations," which represents specific time points in the lifetime of the cell line. The third component integrates the first two patent components to facilitate flagging multiple cell populations affected by a single mislabeled or contaminated cell population, instead of identifying a single population alone. Cell populations with genetic profiles are genetically verified if they match the genetic identity of their cell line and are absent contamination. Cell populations on a path in the tree between two genetically verified cultures are automatically verified without the need for DNA information for each. A cell population is flagged as a potential anomaly if there is an undirected path from a genetically anomalous population to itself that does not pass through a genetically verified population. Therefore, not all cell populations need to have genetic profiles.

BRIEF DESCRIPTION OF THE DRAWINGS

FIGS. 2 to 4A-4B are examples of methods for classifying a cell population in accordance with an embodiment of the present invention.

FIG. 5 is an example of a cell line lineage tree as analyzed in accordance with a method according to an embodiment of the present invention.

DETAILED DESCRIPTION

Figure 1:
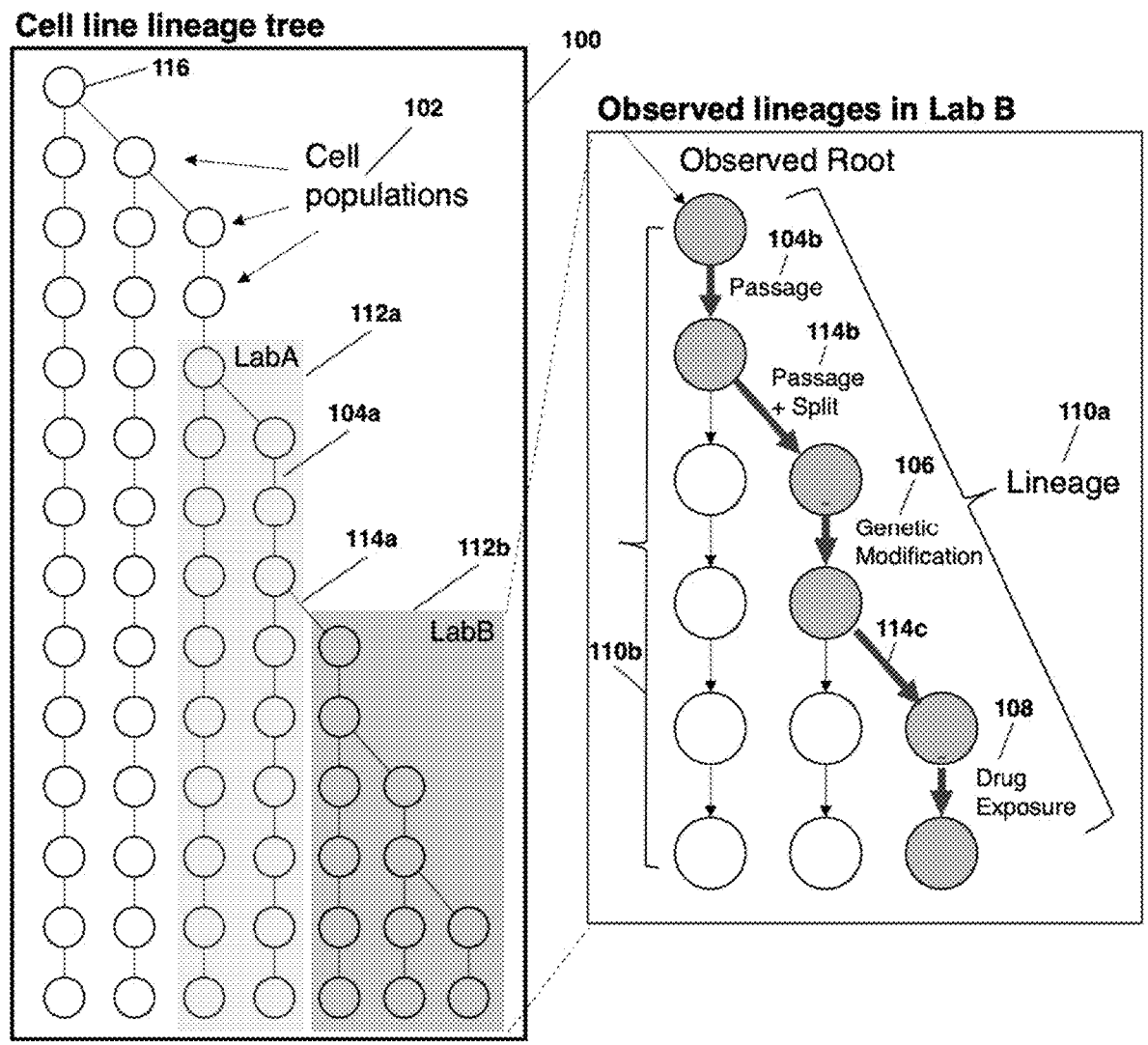
FIG. 1 is a schematic diagram showing an example of a cell line lineage tree in connection with an embodiment of the present invention.

FIG. 1 provides an illustration of terminology used. By "cell line," we mean cell tissue that has been derived from a single person and can proliferate in an in vitro state. It constitutes a collection of relational "cell populations" during its in vitro time [100]. By "cell population," we mean a specific collection of in vitro-grown cells from a cell line at a particular point in time [102]. Cell populations in a given cell line are related to each other by the act of passaging, genetic modification, or conducting a freezing/thaw cycle. By "passaging," we mean the act of taking a subset of cells from a cell population and moving it to a new container [104a and b are examples]. Cell lines are composed of cell populations forming lineage paths that can trace their way back to the same original cells from the patient cell tissue sample [110a, 110b]. By "performing modification," [106] we mean the act of introducing a change in the genetic composition of a cell population, including, but not limited to, a lentiviral insertion or CRISPR/cas9 edit. By "treatment"

we mean the act of introducing an environmental or genetic change (with unknown effects) on the cell population (can include media, irradiation, addition of a drug, etc). And by "conducting a freeze/thaw cycle," we mean the act of freezing a cell population at −80° C. for a period of time, then subsequently thawing and reviving the cells, or subset of cells, by thawing at a later date. The act of these continuous subsequent actions (including passages, treatment, modifications, freeze/thaw) results in a "cell lineage" [110a and b are examples]. The act of a "passage and split" in two or more separate containers is the continuation of the cell lineage, and the creation of a novel lineage [114a, b and c]. Lineages continue upon sharing of a cell population between laboratories. The act of sharing/selling between laboratories creates connected segments within the directed tree [112a and b]. The level of data access between the laboratory segments is determined by data security needs and setting of each.

By genetically validating user-filled cell lineages, the proposed invention is superior to conventional laboratory management software which relies on accurate user input and tube tracking (such as LIMS). The proposed system provides means to flag aberrancies (e.g., mislabeling, cell contamination, and the like) in current cell populations, and leverages the lineage tree to flag other related cell populations as at risk, if appropriate. The genetic analysis of a single cell population combined with tracking cell lineages enables flagging of previous, and parallel, cell populations; DNA sequenced and not sequenced. The system increases the impact of a single DNA analysis beyond the measurement of that cell population at that particular time point, in direct contrast with current approaches.

The method provides several advantages over DNA-profiling services. By tracking cell lineages, putatively mislabeled or contaminated samples without genetic data can be flagged for future verification. The current state of the art compares a generic "cell sample" to a single genetic reference "cell sample"—a one-to-one comparison—and does not consider cell populations as individual entities within a living and evolving system, such as proliferating cell lines. Furthermore, the system facilitates the use of alternative sequencing technologies. For instance, integration of portable DNA sequencers (e.g MinION by Oxford Nanopore technologies) allows laboratory technicians to verify their cell lines rapidly in the lab.

In one example of the method, a cell line and its lineages, cell populations, DNA data and metadata are stored as a "directed tree" (a directed acyclic graph whose corresponding undirected graph is connected and acyclic). Each new cell line has its own graph [100]. Nodes in the tree represent cell populations [102], while edges represent the creation of new populations through events such as passaging to a new petri dish [104a and b], performing a genetic modification [106], or a drug treatment applied to the petri dish [108]. A unique chain of cell populations forms a cell lineage [110a or 110b]. The process of sharing creates segments with the larger cell line tree [112a and 112b]. When users start tracking a new cell line within the computing system, they upload the genetic profile (root) [116]. The genetic profile can either be a list of bi-allelic genotypes at specific positions in the genome, or hemizygous alleles from low-coverage DNA sequencing. As cell populations are periodically added to the computer system, DNA profiles of new cell populations can be uploaded optionally too. For example, a laboratory technician may run a portable DNA sequencer once every five consecutive cell populations. The collected DNA data for that cell population can be directly uploaded to the computer system. This new DNA profile is tested against the genetic root profile of the cell line, and in relation to the other cell populations. If the new genetic profile fails to match the cell line profile, the system flags the cell population as anomalous. The system flags possible anomalies in other cell populations by searching through the tree.

In another example of the system, multiple cell populations in a tree are flagged for potential contamination. User provided cell line data is stored as a directed tree. Users periodically upload genetic profiles of cell populations, which the system uses to check for contamination by looking for mixtures of cell line DNA profiles. The system flags a cell population as an anomaly when it detects contamination by genetic analysis. Contamination is heterogenous by nature (mixture of >2 populations, with an unknown ratio), with an exception being the full overtake of the cell line by a contaminant cell line. If the amount of contamination passes a tolerance ratio for contamination, the system flags the cell population as anomalous and searches the tree to flag other possible anomalies. The system recommends minimal set of cell populations to genetically verify to resolve potential anomalies. Otherwise, if the amount of contamination does not pass the tolerance threshold, the user is advised on a timeframe to retest the population.

In another example, a scientific group (A) gives a cell population to a colleague laboratory (B). Upon mutual agreement, lab B can retrieve the cell lineage history about the cell population, including date cell line was established, number of passages, laboratory procedures, genetic modifications of cell populations, and drug treatments, if applicable. Laboratory B can see when the last genetic test is done, Laboratory B can also generate their own DNA profile for the cell population, and query against the root (from lab A), while creating their own cell line's DNA profile for ongoing analysis.

Component 1 of 3: Genetic Verification from Low-Coverage Sequencing

In this section, we describe a method for genetically verifying cell lines from low-coverage, error prone, DNA sequencing reads. The method is comprised of three steps. In the first step, allele frequencies for genome-wide single nucleotide polymorphisms (SNPs) are estimated from a reference panel. A subset of SNPs is retained by filtering out SNPs with low mean allele frequency. In the second step, a genetic profile for a cell line is constructed using genotypes or hemizygous alleles at a subset of SNPs identified in the first step. The third step consists of probabilistic matching of sequencing reads from a low-coverage DNA sequencing experiment against the reference constructed in step 2.

Deoxyribonucleic acid (DNA) is present in cells of all living organisms. It contains genetic instructions to carry out all of life's essential functions. It is composed of four nucleotides; adenine (A), cytosine (C), guanine (G), and thymine (T) that encode genetic information. The entire collection of DNA for an individual is called their genome. In humans, the genome consists of approximately 3 billion nucleotides organized into sequences along 23 chains called chromosomes. Each person carries two copies of their genome, one copy inherited from her mother and one copy inherited from her father. While the genomes of any two individuals are identical at more than 99.9% of the genetic positions along the genome, 0.1% are different. These differences occur approximately every 1000 nucleotides. A new variant can arise when one nucleotide is substituted for another. These are called single-nucleotide polymorphisms (SNPs) when such a variant is commonly found in a population. Most SNPs have two alleles, or types, corresponding to the nucleotides found at a position. New alleles can spread from one individual to a population as DNA is passed down to offspring from generation to generation by sexual reproduction. Proliferation by cell doubling (or also referred to as cell division) is asexual multiplication of genetic variants.

In humans, the likelihood of shared a genetic variant between two people depends on its frequency in the population and the relatedness of the individuals. Each person has their own, unique, genetic fingerprint determined by the variation in their genome. Thus, patterns of variation are useful for determining genetic identity.

Genetic variation can be assessed using DNA genotyping (e.g., SNP arrays), or DNA sequencing technologies (e.g., nanopore DNA sequencing, pyro sequencing, sequencing-by-synthesis). The former determines specific alleles in a genome, the latter generates DNA sequencing reads: sequences of short chains of nucleotides from an individual's genome. For a method called "shotgun DNA sequencing", a genome is broken up into tiny fragments. The sequenced fragments generate hundreds of thousands to millions of sequencing reads from random positions along the genome. Through sequence alignment one can find where the DNA read came from. The coverage of a sequencing experiment is the number of times a sequencing read "covers" a particular nucleotide in the genome. The present invention is related to low-coverage shotgun DNA sequencing. By low coverage, we mean sequencing to less than an average 1× per nucleotide. The sequencing process is not error free. Therefore, DNA sequencing reads do not always perfectly match the genomic region they originate from.

Given shotgun sequencing reads, we propose a method to test cell lines for genetic identity and contamination against a reference genetic profile.

Figure 2:
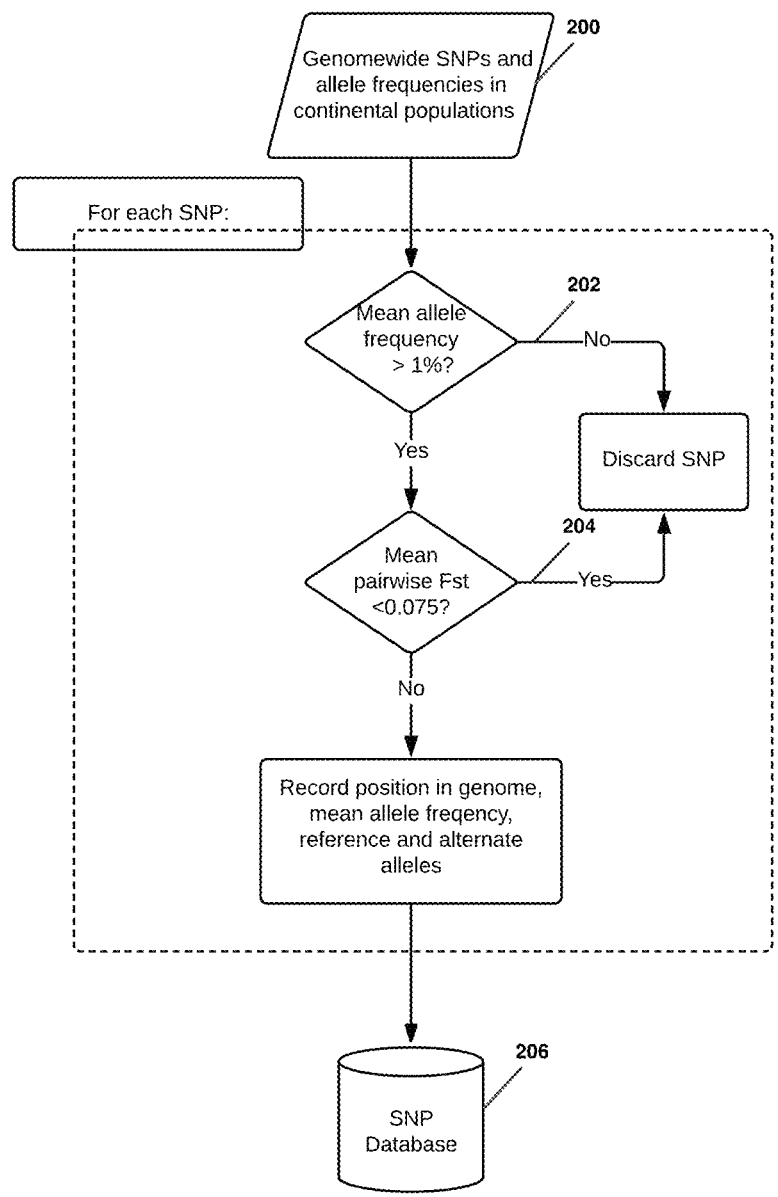

We first build a reference SNP database of a curated of biallelic SNPs by examining their allele frequencies in continental (e.g., African, Admixed American, East Asian, European, South Asian) populations (FIG. 2). These allele frequencies can be computed from a reference panel (e.g., 1000 Genomes), or from reported allele frequencies in a public database (e.g. dbSNP) [200]. Each variant allele at low frequency are likely to be identical across many individuals and should be omitted for DNA identification. We apply two filtering steps that can be executed in any order: a variant allele can be omitted from the database if the mean allele frequency is <1% [202] or, their Fst (a measure for population sub-culture) is too high (can be: >0.075) [204]. The resulting SNP reference database consists of a collection of SNPs that meet the filter criteria, the position in the genome, its allele frequency, and its reference and alternate allele [206].

Figure 3:
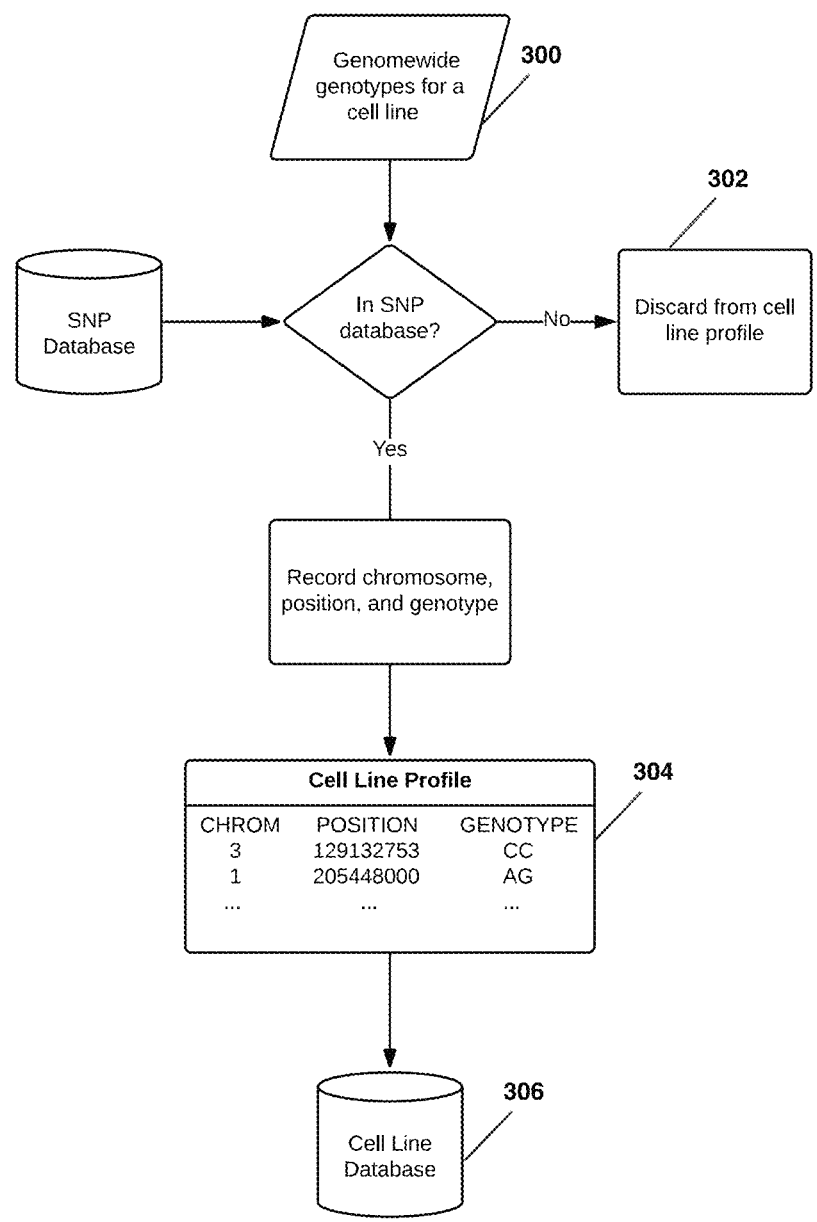

Next we construct a 'cell line profile' (or 'DNA fingerprint') for each individual patient derived cell line (FIG. 3). The DNA profile generated from the cell line can either consist of hemizygous alleles observed from a low-coverage DNA sequencing, genotypes from obtained from a SNP microarray, or genotypes determined from whole-genome DNA sequencing [300]. In each case, the configuration of the cell line profile involves a few steps: observed SNPs are intersected with the SNP database (described in FIG. 2). The SNPs that do not intersect are discarded [302]. The SNPs that do intersect are recorded in a new file, and contains minimally: the chromosome, chromosome position and the genotype [304]. The genetic profile for each cell line consists of a list of genotypes, either 2 alleles (homo- or heterozygous), or a single alleles (hemizygous)). The collection of genetic reference profiles for individual cell lines is stored in a 'cell line database' [306].

Figure 4A:
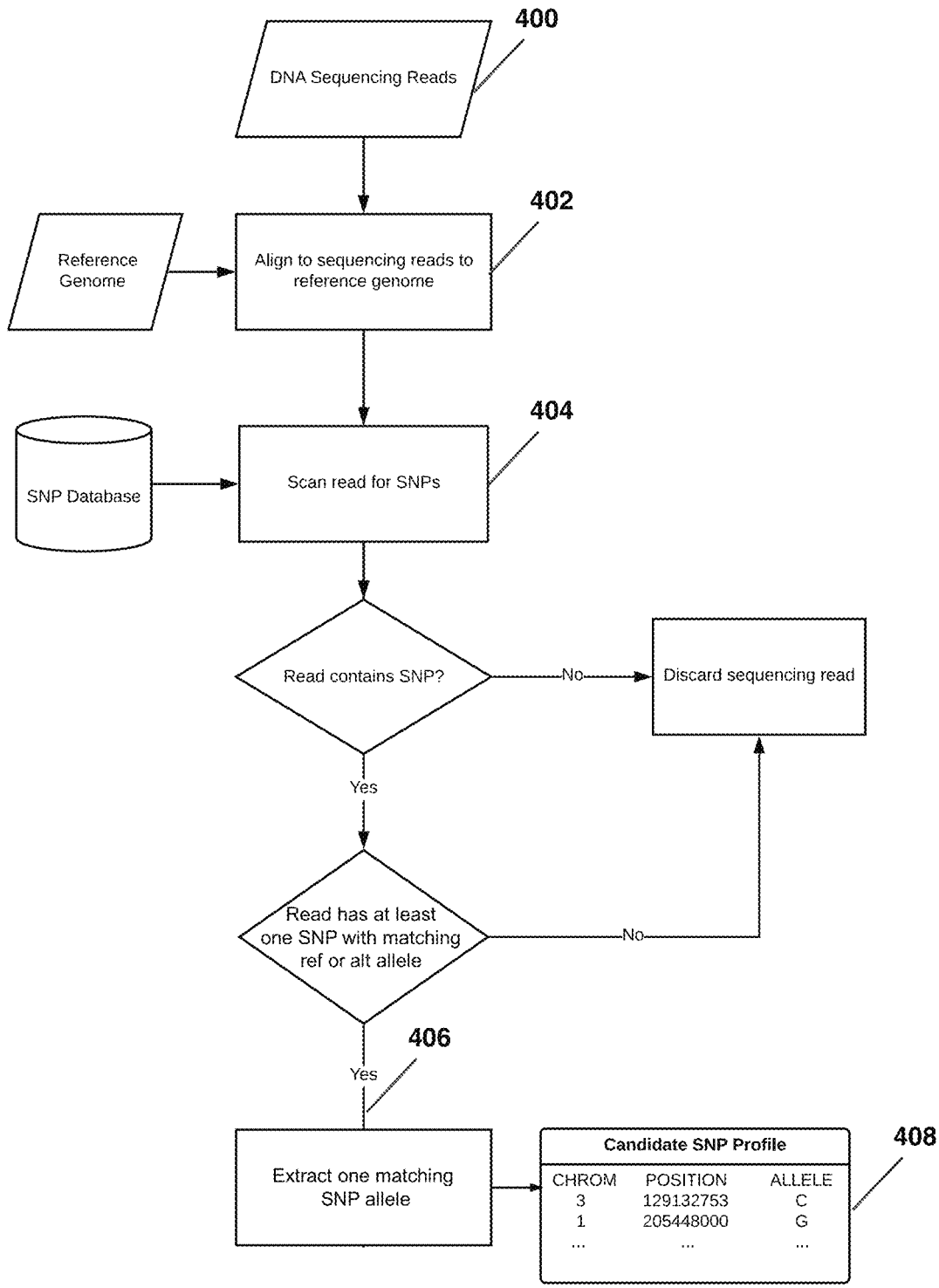

Finally, we describe our probabilistic matching method for low-coverage DNA sequencing experiments of cell populations against reference cell line profiles. We first compile a candidate SNP profile for the cell population (FIG. 4). Sequencing reads are mapped against a reference genome (e.g., Hg19), which is used to extract the coordinates of nucleotides in that DNA read [402]. The SNP database is then searched for a matching SNPs based on these coordinates [404]. Only hemizygous alleles that overlap with SNPs in the database, and match the reference or alternate allele, are retained [406]. The remaining nucleotides are discarded. The SNP position is then intersected with the SNP position of a candidate reference profile in the cell line database [408]. If a corresponding hemizygous allele or genotype is found, the SNP is used in the probabilistic model below.

Probabilistic Model. The probabilistic model for matching the obtained hemizygous alleles against a reference cell line profile is as follows. Suppose we sequence L hemizygous alleles from an unknown cell population, $x_1, x_2, \ldots, x_L$ where $x_l \in \{0, 1\}$ gives number of reference alleles observed at locus l. We wish to compute the likelihood and posterior probability that the cell population matches the reference. Call an observed allele a hit if it is concordant with the reference sample, and a miss otherwise. We count the number of misses. Let $$Y_l = \begin{cases} 1 & \text{observed allele l is a miss} \\ 0 & \text{otherwise} \end{cases}$$

$$Z_L := Y_1 + Y_2 + \ldots + Y_L$$

Thus, $Z_L$ counts the total number of misses after L alleles are observed. Note that the only time a miss can occur is when the reference is homozygous for one allele, but the alternate allele is observed. Let g be the genotype of the reference, A be the reference allele, and B be the alternate allele. Further, let $f_A$ and $f_B = (1-f_A)$ be the allele frequencies of the reference and nonreference alleles respectively.

Denote match types by E for exact, R for a random individual. Then, given an error rate ∈, the probability of a miss at a locus given a match and a random individual is $Pr(Y_l=1|E, g=AA) = \in$ $Pr(Y_l=1|E, g=BB) = \in$ $Pr(Y_l=1|R, g=AA) = f_A \in + f_B(1-\in)$ $Pr(Y_l=1|R, g=BB) = f_B \in + f_A(1-\in)$ Now suppose the sample was contaminated. That is, it is a mixture of the reference sample with some unknown sample. Suppose C percent of the mixture is from the reference and 1−C is from an unknown source. Then the probability of a miss at a locus, for an exact match, changes to $Pr(Y_l=1|E,g=AA)=C\epsilon+(1-C)(f_A\epsilon+f_B(1-\epsilon))$ $Pr(Y_l=1|E,g=BB)=C\epsilon+(1-C)(f_B\epsilon+f_A(1-\epsilon))$ The probability of a random match remains the same. We investigate contamination at specified thresholds $$C \in \left\{1, \frac{1}{2}, \frac{1}{4}\right\},$$

though we are not limited to precisely these thresholds. C=1 corresponds to absence of contamination.

For a hemizygous genetic reference, with reference allele $a \in \{A, B\}$, these probabilities become $$Pr(Y_l = 1 | E, a = A) = \frac{1}{2}\epsilon + \frac{1}{2}(f_A\epsilon + f_B(1-\epsilon))$$

$$Pr(Y_l = 1 | E, a = B) = \frac{1}{2}\epsilon + \frac{1}{2}(f_B\epsilon + f_A(1-\epsilon))$$

$$Pr(Y_l = 1 | R, a = A) = f_B\epsilon + f_A(1-\epsilon)$$

$$Pr(Y_l = 1 | R, a = B) = f_A\epsilon + f_B(1-\epsilon)$$

And with contamination at 1−C percent they are $Pr(Y_l = 1 | E, a = A) =$ $$(1-C)\left(\frac{1}{2}\epsilon + \frac{1}{2}(f_A\epsilon + f_B(1-\epsilon))\right) + C(f_B(1-\epsilon) + f_A\epsilon)$$

$Pr(Y_l = 1 | E, a = B) =$ $$(1-C)\left(\frac{1}{2}\epsilon + \frac{1}{2}(f_B\epsilon + f_A(1-\epsilon))\right) + C(f_A(1-\epsilon) + f_B\epsilon)$$

Inference of Genetic Identify and Contamination. Suppose we have observed m misses out of L alleles. We wish to compute the model likelihood given a degree of contamination, C:

$Pr(Z_L=m|C).$ and also the posterior distribution on the degree of relatedness:

$$Pr(C | Z_L = m) = \frac{Pr(Z_L = m | C)Pr(C)}{Pr(Z_L = m)}$$

We can compute the likelihood recursively using the following relation $Pr(Z_L=m|C)=Pr(Y_L=1|C)Pr(Z_{L-1}=m-1|C)+Pr(Y_L=0|C)Pr(Z_{L-1}=m|C)$ Once $Pr(Z_L=m|C)$ has been computed for each C, we can compute the posterior distribution. The denominator of the posterior can be computed as follows.

$$Pr(Z_L = m) = \sum_{C \in \{1, \frac{1}{2}, \frac{1}{4}\}} Pr(Z_L = m | C)Pr(C)$$

In practice, $Pr(Z_L=m|C)$ can be computed for each locus using dynamic programming by storing the result for each l as they are observed and updating $Pr(Z_L=m|C)$ using the above recurrence.

Our model also facilitates approximate inference using a normal approximation. That is, given L observed sites, the first two moments of $Z_L$ are:

$$\mathbb{E}[Z_L] = \sum_{l=1}^{L}\mathbb{E}[Y_l] = \sum_{l=1}^{L}Pr(Y_l = 1 | C, g)$$

$$\text{Var}(Z_L) = \sum_{l=1}^{L}\text{Var}(Y_l) = \sum_{l=1}^{L}Pr(Y_l = 1 | C, g)(1 - Pr(Y_l = 1 | C, g))$$

Thus, we can approximate the distribution of $Z_L$ by $Z_L \sim \text{Normal}(\mathbb{E}[Z_L], \text{Var}(Z_L))$ This computation is more efficient than the exact calculation and can be used to quickly pare down the database by quickly eliminating random individuals from potential matches.

Flagging Samples. Samples are flagged if the posterior probability of a match given a reference is below a set threshold (for example <0.99). Furthermore, samples are flagged as contaminated if the posterior probability under a proportion of contamination is high (for example >0.75).

Figure 4B:
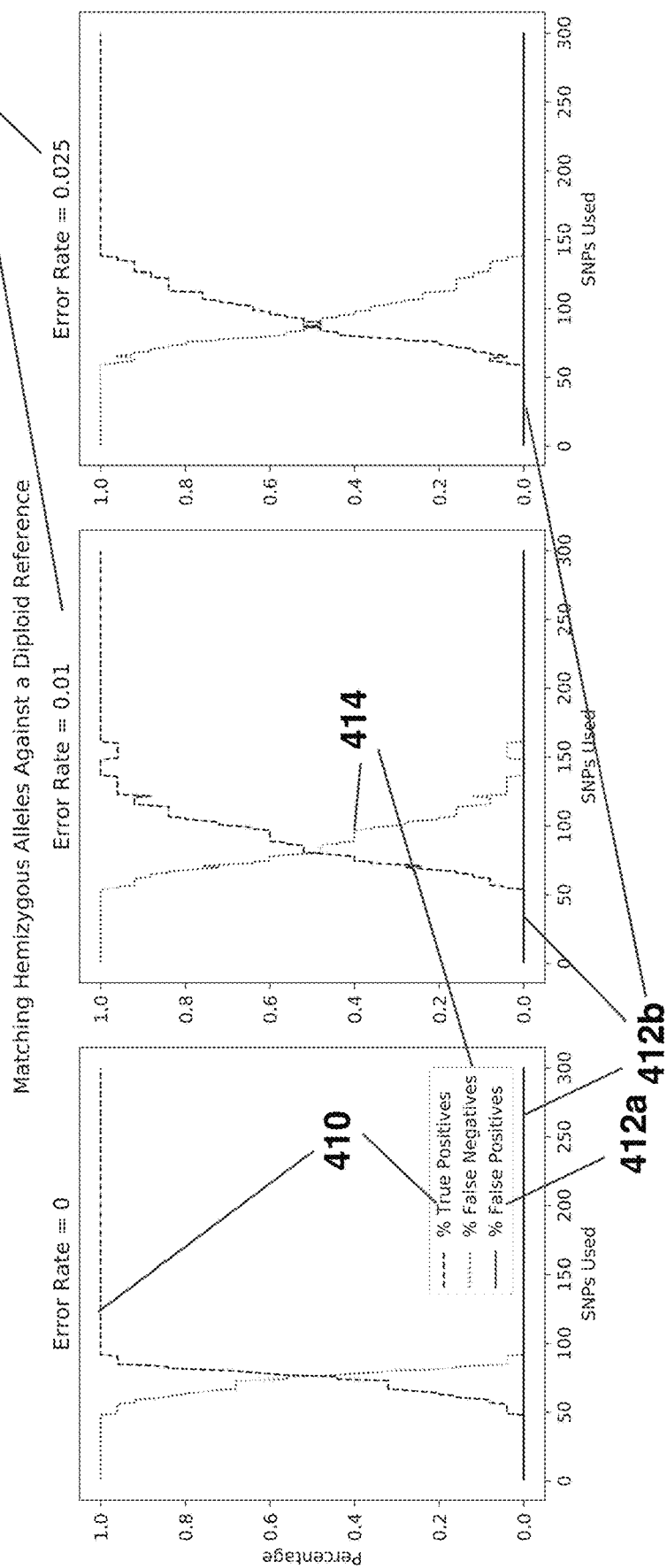

To demonstrate how match probabilities under our model can be used to match hemizygous alleles against a reference, we performed a simulation experiment using semi-synthetic data (FIG. 4b). We first created a reference SNP database by computing allele frequencies in continental populations from individuals in the 1000 Genomes Project. We filtered out SNPs with mean pairwise Fst <0.075 or mean allele frequency <0.05, and collected the remaining SNPs in our SNP database.

Next, to generate a realistic reference cell line database, we downloaded 25 SNP profiles from OpenSNP. Each profile contained approximately 950,000 genotypes at locations across the genome. For each individual, we simulated a candidate SNP profile of hemizygous alleles by selecting a subset of randomly chosen genotypes and extracting one allele from each genotype. We additionally simulated sequencing errors by randomly changing each allele in the candidate SNP profile with probability E (error rate). We used simulated candidate SNP profiles to compute the probability of a match to each reference profile in the cell line database, varying the number of SNPs used to identify genetic matches. Thus, we computed match probabilities 25 matching hemizygous profiles, and 25×25=25=600 mismatching profiles.

FIG. 4b displays the percentage of correctly identified samples (true positives) [410], misidentified samples (false positives) [412 a and b], and unidentified samples (false negatives) [414]. Across all error rates [416] we explored, <200 SNPs was sufficient to reidentify all hemizygous candidate SNP profiles. Moreover, no SNP profiles were misidentified.

Once a cell population is verified, the low-coverage data can be used to append and extend the reference cell line profile, if novel SNP sites/alleles are encountered. This is done through the process described in FIG. 3. Even though it is not default in the system, aggregating data can be achieved upon compiling data from consecutive cell populations. Application examples include: reducing computing cost per inferred matching attempt, reducing the number of reads required to obtain the critical number intersecting reads (reduced reads leads to lower DNA sequencing cost).

Component 2 of 3: Method for Tracking Cell Line Lineages

We propose an approach for tracking cell populations in a cell line by storing relationships between populations as a directed tree. In graph theory, a graph $G=(V, E)$ consists of a set of vertices V and edges $E \subset V \times V$ denoting relationships between vertices. For directed graphs, E is a set of directed tuples $(i,j) \in E$ where $j \in V$ is descended from i. For undirected graphs, E consists of sets $\{i, j\} \in E$ that denote a link between $i,j \in V$.

In an application to cell lines, V is a collection of cell populations [102] in a cell line [100], and E describes the relationship between cell populations [104, 106, 108, 114]. The tuple (i,j) describes the relationship that cell population $j \in V$ is descendent from $i \in V$ in some sense, for example through passaging [104] or performing a genetic modification [106].

Our method to track a cell line is as follows. For each cell line tracked, we instantiate a new graph $G=(V, E)$. This graph initially contains a single cell population obtained by a lab, typically from an external service.

Multiple graphs can exist for the same cell line. This would occur, for example, when a laboratory obtains cell populations from a cell line from two external sources. Laboratory procedures such as passaging, performing an experiment, performing a genetic modification, or freezing then thawing a cell population correspond to adding new populations to V. New populations are linked together by adding an edge (i, j) from the parent population i to its descendant j.

Component 3 of 3: Integrating Genetic Verification with Cell Line Tracking

Importantly, to each cell line graph G we associate a reference genetic profile of the cell line (configuration described in FIG. 3). Furthermore, cell population in G can be associated with a genetic profile obtained from a low-coverage sequencing experiment described in "GENETIC VERIFICATION FROM LOW-COVERAGE SEQUENCING." Cell populations with genetic profiles that match the reference and are absent of contamination are called "verified." Specifically, they are genetically verified with respect to the algorithms previously described. Cell lines that are flagged for contamination or that do not match the genetic reference are called "anomalies."

By tracking the graph structure of a cell line, we can verify cell populations that do not have genetic profiles by traversing the graph (e.g. going up into the graph). Furthermore, we similarly flag cell populations without genetic profiles as potential anomalies. FIG. 5 provides an illustration of this process in a hypothetical computer system. The computer system stores a graph of the cell line, along with genetic profiles. The figure depicts a directed tree of a single cell line [500]. Cell populations are circles (vertices), and directed edges are depicted by direct arrows. The root of this tree, at the top of a figure, has an incoming edge [502]. This illustrates that the root cell population is part of a larger unrecorded graph. Cell populations with genetic profiles can be depicted as shaded circles [504] and verified cell populations can be specified by a checkmark [506].

The cell populations that exist on a directed path between any two genetically verified cell populations are "auto-verified," even if they do not have their own genetic profiles. This path can be found using standard algorithms for graph traversal, such as breadth-first search or depth-first search. For example, two cell populations are genetically verified [504], and the cell populations on the path between them are also auto-verified [506]. Continuing with the example, suppose a new genetic profile for a cell population is created that is flagged as anomalous by the algorithms in section "GENETIC VERIFICATION FROM LOW-COVERAGE SEQUENCING" [508]. The set of all undirected paths (i.e. paths that do not need to obey the directionality of an edge) from the anomaly that do not cross a genetically verified population are potentially anomalous [510], depicted in this figure by black dots. Potential anomalies can be resolved by creating another genetic profile [512], for a different cell population, that expands the number of paths between genetically verified lineages. In the illustration, a new genetic profile resolves a subset of potential anomalies because it creates a new path between two genetically verified lineages [514]. Here, two cell populations are identified as anomalies [516], and experiments performed those will unlikely result in the same results as the correct, verified cell populations.

In our system we advise the user which cell population provides the most optimal and cost efficient verification path.

In summary, by combining our method of genetic verification with our method of tracking cell lines, we can verify cell populations that do not have genetic profiles. Furthermore, we can flag potential anomalies in cell populations that do not have genetic profiles.

Examples: A Computer System for Managing and Monitoring Cell Lines

Figure 6:
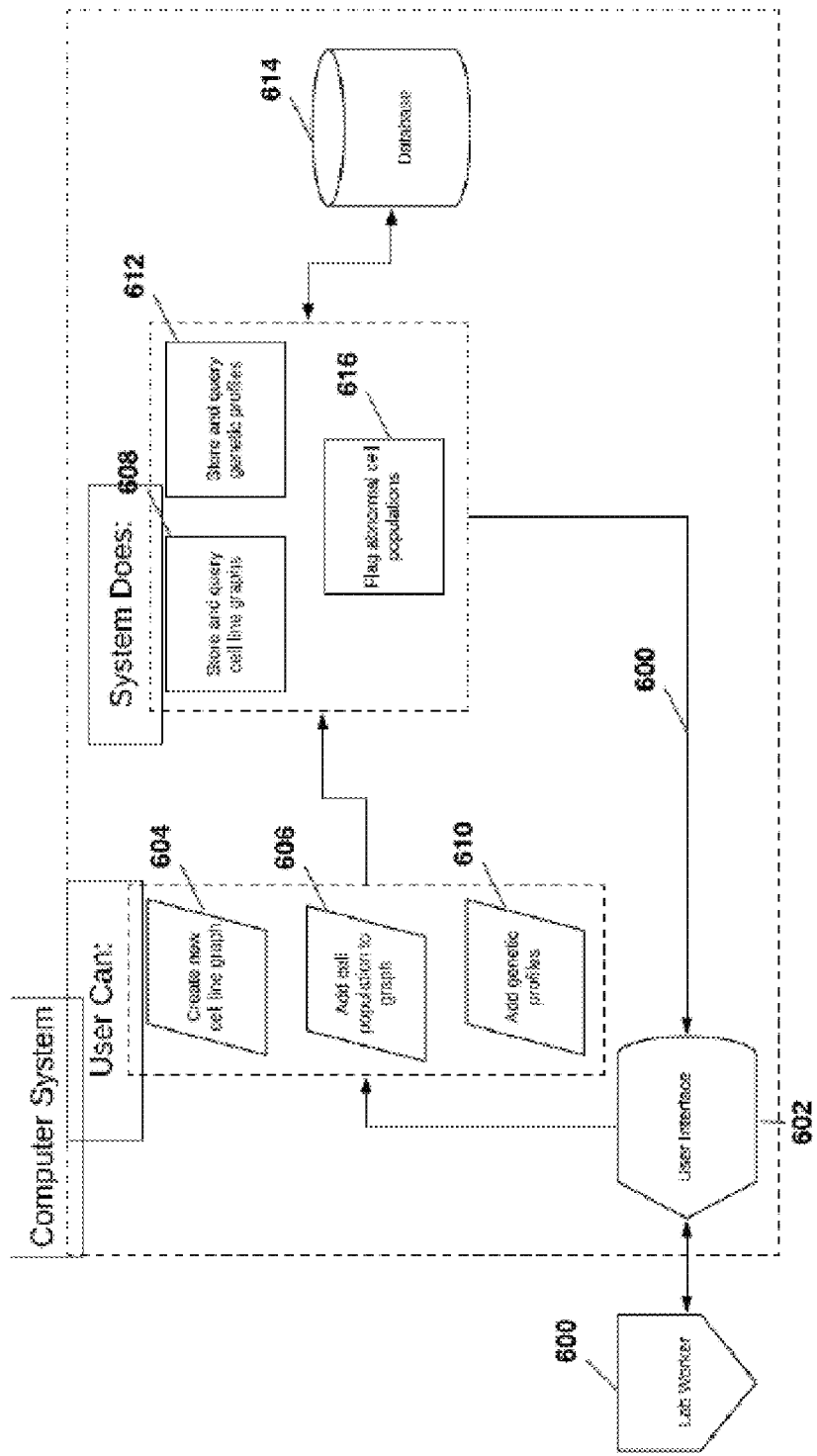
FIG. 6 is a schematic example of an example of a system in accordance with an embodiment of the present invention.

In this section we describe an example of how the present invention can be used in a computer system to track and manage cell lines. FIG. 6 provides a schematic overview of a computer system. A user of the system [600]—which can be any laboratory worker; laboratory manager, laboratory technician, postdoctoral researcher—tracks a cell line by creating a corresponding entry in the cell line management system through its user interface [602]. Each time a cell line is acquired in the lab, the user can create an entry for that particular cell line [604] and the corresponding DNA profile [610], [614]. The user can further identify how the cell population they work with relates to previously entered populations, if they exist, by providing information about passages, modifications, treatments, and freeze/thaw cycles [606]. This links cell populations together in the same cell line graph [608]. The management system uses this information to create a comprehensive description of the lineage of all cell populations in the cell line. Furthermore, the user can choose to add [610], query [612] and store [614] genetic information for each consecutive cell population to verify relationships between cell populations. The system reports genetically identified abnormalities over time in relation to stored previous time points and/or cell populations [614]. The user can choose to catalogue information regarding cell behavior, cell health, protocol adjustments, and/or enter novel protocols [614]. The system reports identified abnormalities. The computer system can either exist as a program on a single computer, or on a server accessed by a web interface.

Figure 7:
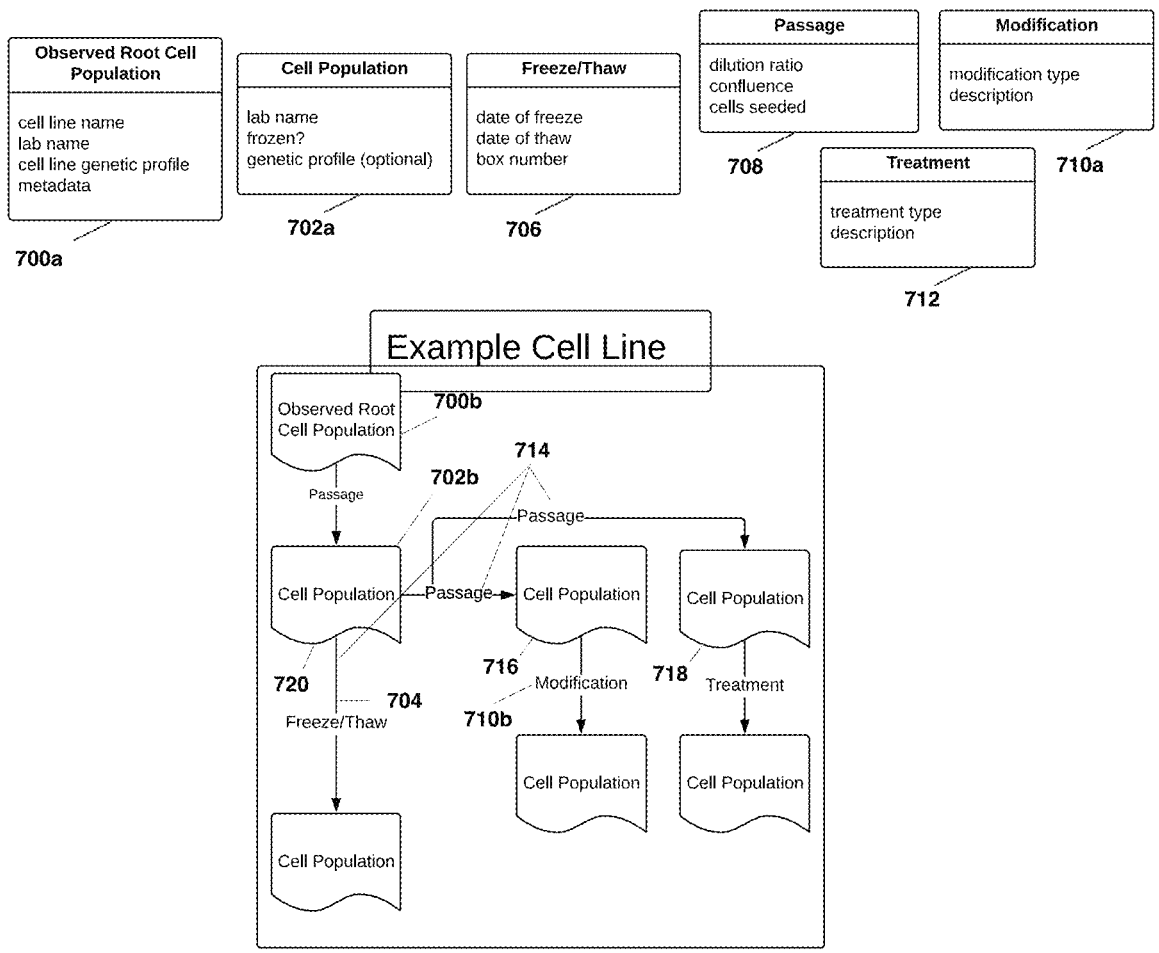
FIG. 7 is a schematic of an example of using an embodiment of the present invention on a sample cell line.

FIG. 7 provides an example, in a flow diagram-like format, of how the system tracks relationships between cell populations over time in a hypothetical cell line. For each cell line, the user uploads a root cell population—the first population entered into the system [700a, b]. The root cell population contains information on the particular cell line; for instance, the common name for that cell line, a user provided name, laboratory specific metadata, and a genetic profile for the cell line (or cell population). Each subsequently uploaded cell population contains a laboratory provided name and can be provided with an optional genetic profile. The relationships between cell populations is structured as a directed tree. The vertices in the graph are the cell populations within the cell line [702 a and b], and edges give relationships between cell populations [704 and 706 for example]. The user specifies relationships between cell populations by adding edges to the graph, while new cell populations add nodes. Each cell population is connected by an edge, which can be a freeze/thaw cycle [706], a passage [708], a modification [710], a treatment [712], or other. Each edge type that defines a kind of relationship can have associated metadata that more particularly defines the relationship and facilitates cell line management. For example, to track a cancer cell line, the metadata about the root is stored (name of the cell line, information on cancer type and tissue, genetic profile), subsequent passages can contain information about cell growth characteristics (number of cells seeded, doubling speed), media protocols and/or the type of passage (monoclonal versus polyclonal) [708], split schemes used to generate new cell lineages [714]. In this example, one new lineage [716] is subjected to a genetic modification [710], (for example, to change a single locus in the genome to eventually test if that changes the responsiveness to specific drugs). Metadata about this modification can contain information about the genetic engineering design; targeted insertions, deletions, or edits. Or is describes the method of modification, such as by lentiviral, CRISPR/cas9 or some other vehicle for modification [710a and 710b]]. The second lineage of the cancer cell line [718], the user wants to perform a drug treatment to understand how the cell population responds (for example, if this cell line was a cancer cell line, this step could function to understand if the drug is effectively impairs its growth) Finally, the third cell lineage gets frozen [720], to be thawed at a later stage. Freeze/thaw edges can contain information about the freeze date, the thaw date, as well as laboratory specific metadata about such things as a storage container or storage medium that has been used for the cell population [706]. The metadata is stored and analyzed in comparison to the historical cell populations in the lineage or between lineages.

Figure 8:
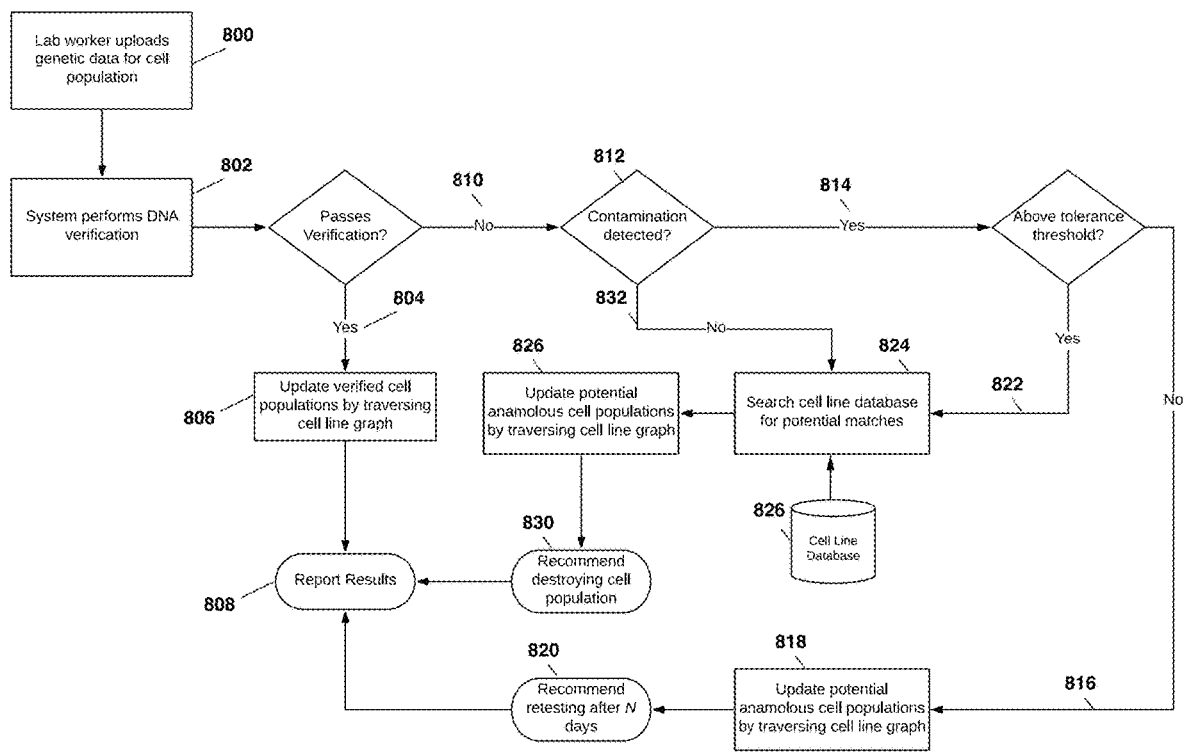
FIGS. 8 and 9 are exemplary methods for practicing an embodiment of the present invention.

FIG. 8 provides an exemplary flow diagram for how the system can integrate genetic information. For example, a user can upload DNA sequencing data from a low-coverage sequencing experiment and associate it to a specific cell population [800]. Note that the cell population is part of the tree, and therefore contains the prior assumption to which cell line it belongs (the 'expected cell line'). By using the methods described "GENETIC VERIFICATION FROM LOW-COVERAGE SEQUENCING," the cell population is genetically verified to match against the expected cell line and to determine the likely contamination load [802]. If the cell population is successfully verified to match the assumed cell line [804], the system traverses the cell line graph to verify other cell populations without sequencing data [806, and FIG. 5]. Results are presented to the user by the GUI [808].

Alternatively, the cell population does not pass verification [810]. Failure to match the expected cell line can mean two possible scenarios: 1) full overtake of alternate cell line (by mislabeling, or fully overgrown by alternate cell line), or 2) a possible mixture of cell line and alternate cell line. The likelihood is tested by our contamination algorithms [812]. If the system detects a mixture [814], it will continue to determine if it is above tolerance threshold.

If the contaminant is below threshold [816], the cell population is flagged as suspect, and traversing the graph non-tested but related cell populations are also marked as potentially anomalous [818]. The system returns to the user after how many days he/she should genetically test the next cell population in that lineage [820], or related cell population.

If the contamination is above threshold [822], the system will test if the contaminant cells are known by trying to match the genetic profile [824] to the entire cell line database [826]. If identified, the graph is traversed and additional cell populations are marked as suspect anomalous and flagged for further testing [828], the system can return to destroy the current cell population [830].

If the system does not detect a cell mixture [832], the algorithms will search if the alternate cell line can be matched against an entry in the entire cell line database [824]. Go through the motion of flagging other cell populations at risk [826]. System will recommend destroying the cell population. Final results and recommendations are presented in the GUI [808]. In each case, the system uses the methods in "INTEGRATING GENETIC VERIFICATION WITH CELL LINE TRACKING."

Figure 9:
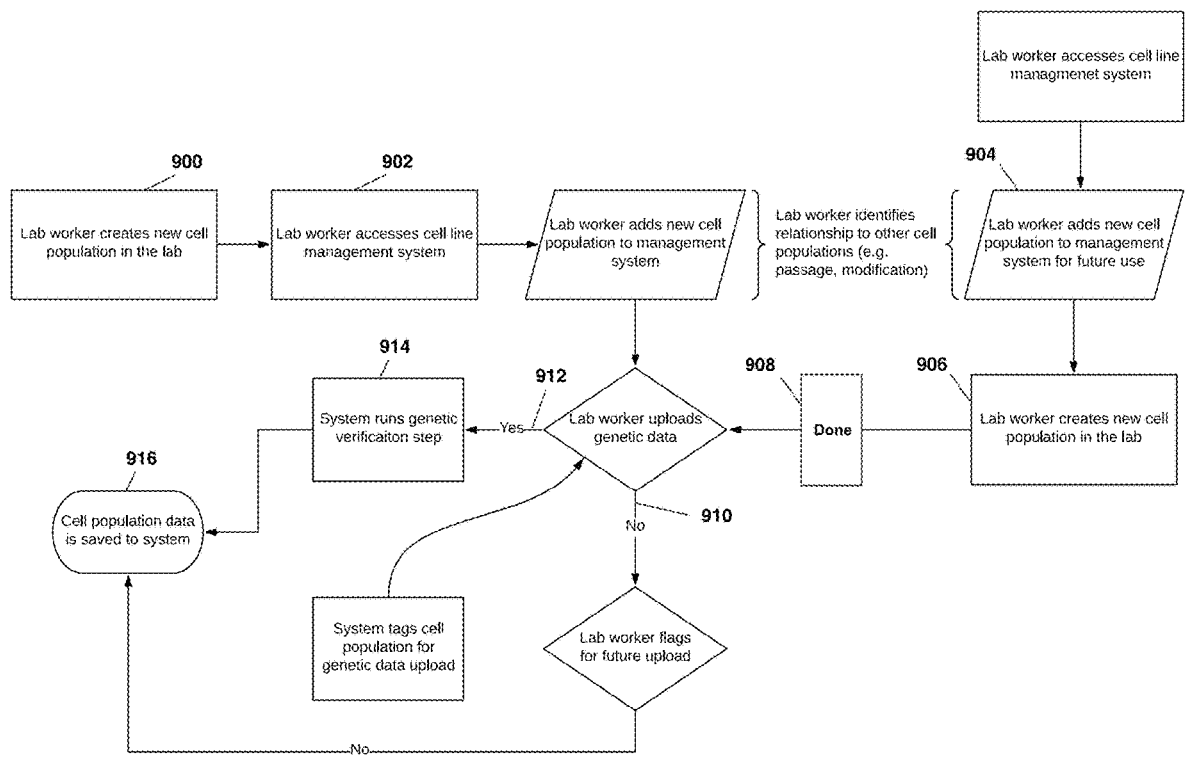

The laboratory worker can use the described embodiment of a management system prior to starting work in the laboratory to guide future passaging strategies, such as making use of an identified most beneficial dilution protocol as identified in the metadata for passaging referred to in connection with FIG. 7. The laboratory worker can also use the system after starting work in the laboratory to verify that passaging, modifications, and freeze/thaw cycles have been completed correctly. FIG. 9 provides exemplary workflows that illustrate how the user could interact with the system and how each component of the system works with the others.

1) In the first example, a laboratory worker updates the cell line management system after completion of the work in the laboratory. He/she creates new cell population in the laboratory [900]. The worker accesses the cell line management system in order to catalog it for tracking [902]. The worker adds the cell population to the management system in the manner previously described (FIG. 6).
2) In the second example, a laboratory worker creates a new entry into the management system prior to starting work in the laboratory to plan a future passage, modification, or freeze/thaw cycle [904]. The laboratory worker then executes the passage, modification, or freeze/thaw cycle in the laboratory [906] and afterwards returns to the system and confirms completion [908].

After the cell population has been added to the system, each workflow proceeds in the same way. The system prompts the user to upload genetic data. If the user does not upload genetic data, the system provides a prompt to optionally tag the cell population for future upload [910]. Once genetic data has been added [912], the system performs genetic verification in the manner previously described [914]. The system stores results and indicated preferences [916] (such as not wishing the upload genetic information for that cell population) to continue tracking and monitoring the cell populations in the cell line.

Figure 10:
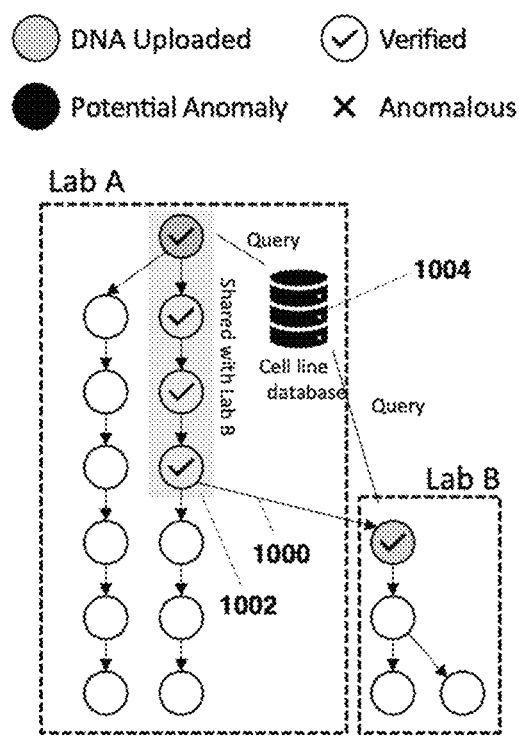
FIG. 10 is an example of an outcome of applying an embodiment of the present invention to an exemplary cell line.

FIG. 10 illustrates an example of how the computer system can be used to share information between organizations. In the example, lab B receives a new cell population from lab A. The system facilitates sharing a subgraph of the cell line from lab A with lab B [1000]. This includes only the lineage information for that cell population (grey box FIG. 10, [1002]). For example, Lab B can see the number of passages from the root in Lab A to their new cell population. Lab B can then query candidate SNP profiles (from sequenced cell populations) against the genetic reference of lab A [1004].

Figure 11:
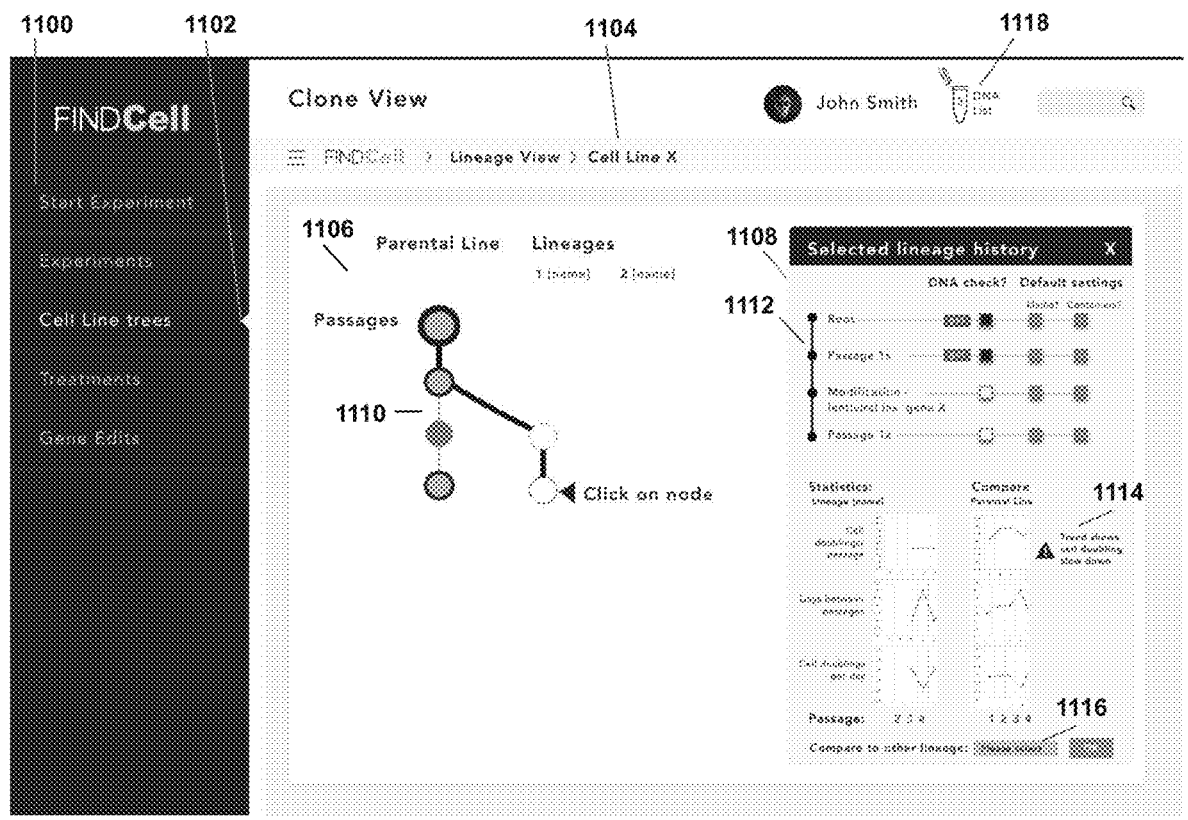
FIGS. 11 to 13 are exemplary user interfaces for use with an embodiment of the present invention

An example of how the system can be implemented in a graphical user interface (GUI) is presented in FIG. 11. The GUI has a menu bar that gives display categories: display by experiment, display by treatment type, display by gene edits [1100]. These (except the cell line tree) can display multiple cell lines under the treatment, modification regime. The lineage tree display [1102] provides the directed tree view for a cell line. In this example, a cell line is selected [1104]. The graphic tree is the center of the screen [1106], additional information and/or cell line statistics can appear pop-up window or bar on the side [1108]. For the graphic tree [1106]: each node represents a cell population, consecutive passages can be added below, vertically (/Y-axis) and connected by a line (edge) indicating information about the event. New lineages are created by splitting a cell population, so it has two descendants [1110]. The user can enter relevant information about the event which will be stored in the databases linked to this particular cell population (as described above). Further passages, or other steps can be entered similarly over time.

By clicking on a node, the cell population and lineage information and trends get displayed [1108]. This summary window displays an overview of genetic, laboratory, and biological trends for that cell lineage. Each step is displayed in order [1112], with relevant statistics. The aberrancies are flagged to the user [1114]. Lineage information goes back to the root if possible, and gives the number of passages, modifications, freeze/thaw events, treatments etc. The user can also track biological behavior of the cell (cell doublings, morphology). The statistics can be directly compared to other cell lineages [1116]—or lines, over time or to similar genetic profiles.

A DNA analysis query is displayed [1118]. In this example, 3 cell populations are in the query for DNA upload (as described in FIG. 9).

The user may decide to add DNA verification to the tree. To do this, the user may right click, the node will be marked (here by a dark ring) [1200] and add the cell population to the DNA-list (tube icon in the top right) [1118, 1208]. By clicking on the icon a list is displayed, which contains multiple cell populations that need DNA analysis. In the laboratory this list provides an easy overview of samples to prepare for DNA sequencing.

Figure 12:
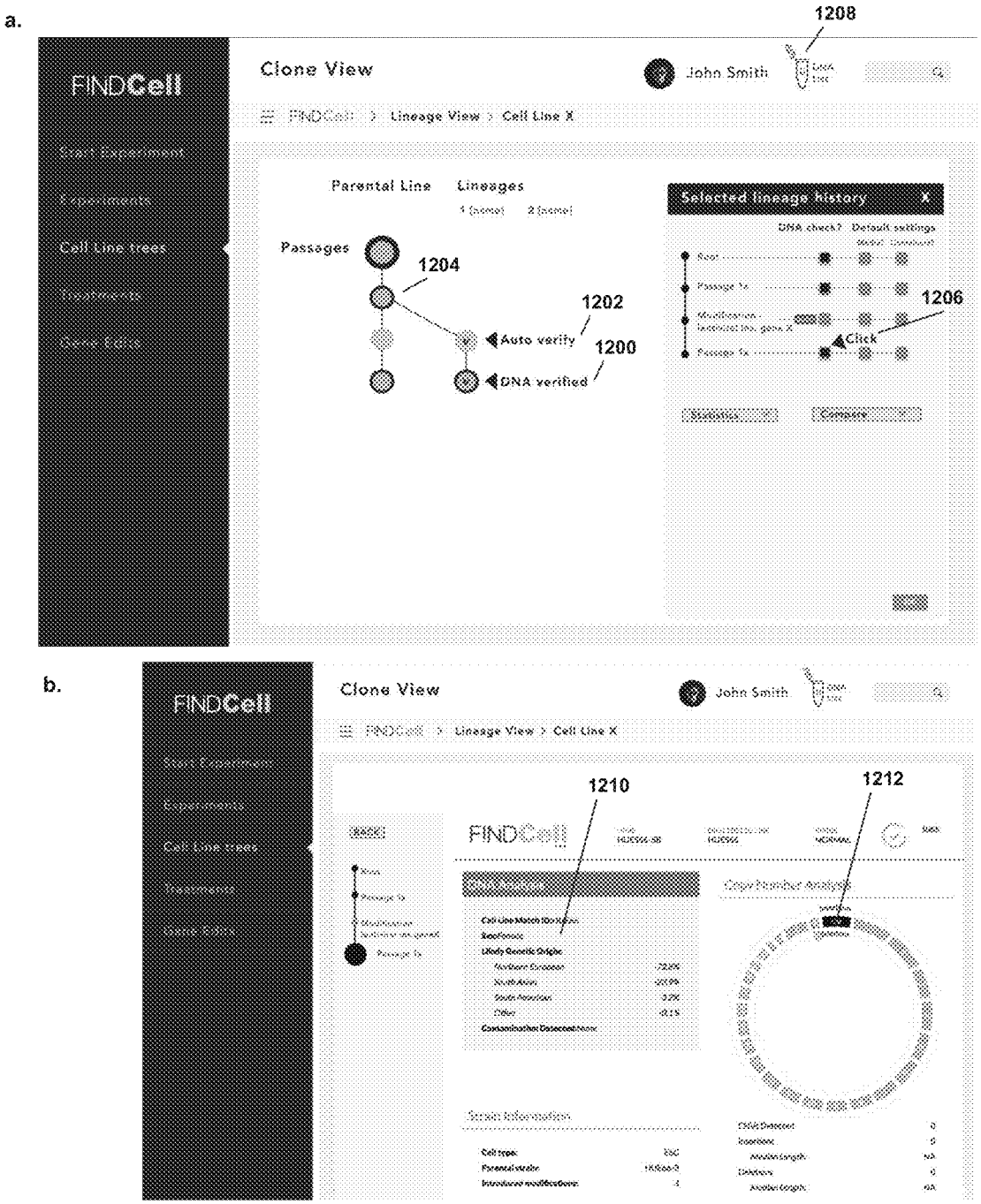

Once the experiment is done, and the DNA information is uploaded, it is linked to the cell population in the tree. The DNA information is used to verify the cell population as described above. If the population is verified, the system traverses the cell graph (looks back up) to verify populations without DNA data (auto-verify), and until it finds the cell population that was last verified [1204]. In this example in FIG. 12, only a single cell population was not DNA verified before and is auto-verified [1202]. Clicking on the node the lineage information is displayed (similar to 1108), after DNA analysis the user can click [1206] to get more information about the genetic status of the cell population in the DNA reports. Note that after analysis of the samples on the list, the DNA list resets to "0" [1208].

DNA reports of each cell population can be reviewed as stand-alone analysis documents. These can include information on identity, ancestry [1210], copy number variation [1212], and other forms of analysis. The DNA results can also be used to compare against other cell populations. Even though DNA is displayed here, these reports can contain DNA, RNA, protein analysis, and the longitudinal comparison results between cell populations and lineages are stored in our databases.

Figure 13:
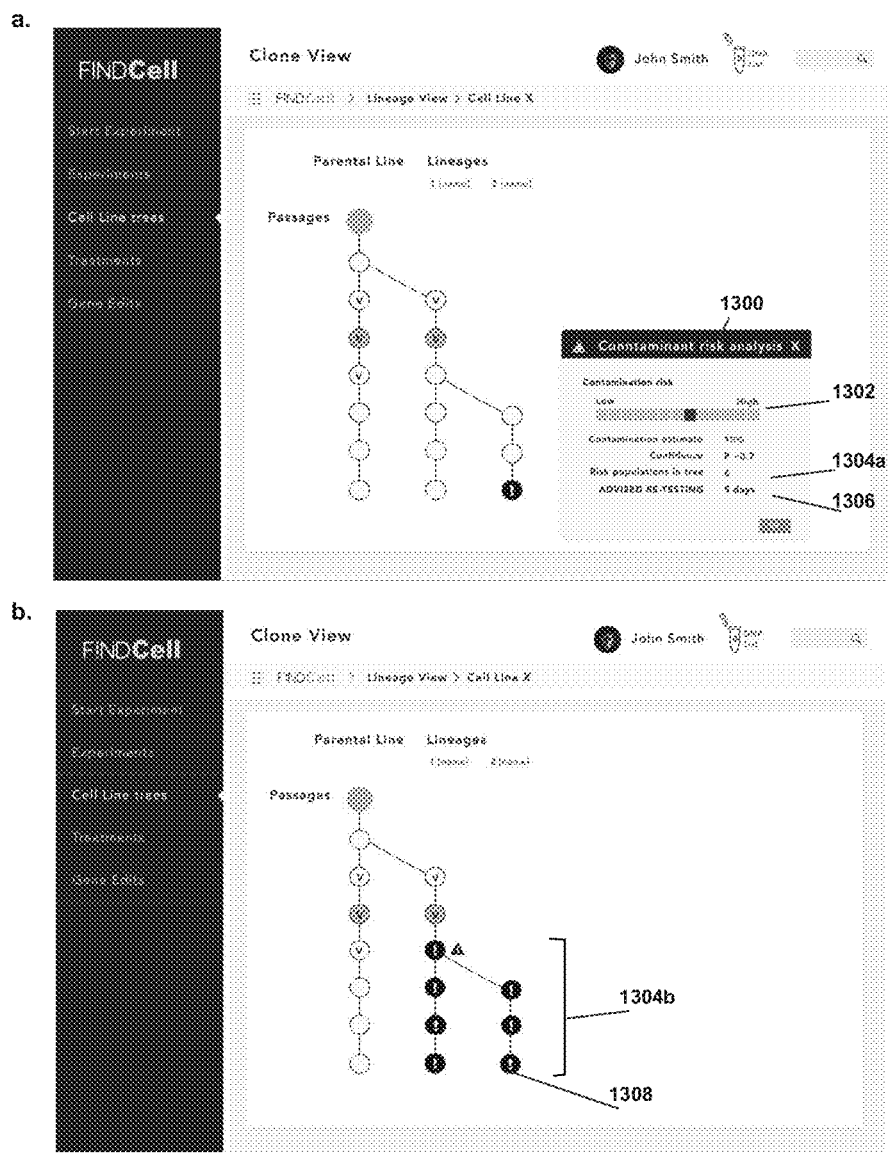

After the user uploads the data the system also returns a contamination probability (FIG. 13). In this example, the risk analysis is in a pop-up window [1300]. The system flags the cell population as suspect and gives the user the risk score [1302], and an additional risk factor for previous cell populations [1304a and 1304b]. The system makes a recommendation for ongoing work [1306]. The system will also attempt to identify the contaminant if it is present in the cell line database (as described in FIG. 8).

Based on the approximation of the contaminant on the cell population (e.g. 10%, 25%, 50%) and the confidence of the call, the system approximates the start of the contamination event if possible or relevant and flags the cell populations as suspect (for example "!" [1308]).

Based on the risk factor, the system advises when to test the next cell population. This depends on the severity of the contaminant and the confidence of the call.

CONCLUSION

Our system enables tracking living systems over time. Here we explicitly describe tracking of cell lines and cell lineages. This system is important for previously developed and characterized cell lines, and also for future work comprising cancer cell line panels, stem cell technologies, and organoids. Our system for tracking cell lines supports optimal operations for drug discovery, to test and validate new targets.

This method allows tracking of contamination by other cell lines but can be extended to tracking and detection of contamination by acquired error during the in vitro state (mutations, copy number differences, or structural differences).

The proposed system can be used for tracking and managing any asexually grown in vitro cell population such as mouse tissue culture, insect cell culture, hamster tissue culture, yeast cells, bacterial cell lineage tracking used in biomedical research. The longitudinal tracking of living cells and organisms can also be applied to the agricultural applications, and the food supply chain, where time points can include contact point of distributors. This patent aims to protect a method to integrate longitudinal management of living systems by using genetic verifications.

The invention claimed is:

1. A method, comprising:
    receiving, at one or more processors, a digital representation of a first cell population;
    receiving, at the one or more processors, a genetic profile of or a genetic test result for said first cell population;
    generating, at the one or more processors, a digital representation of a directed tree associated with the first cell population for a plurality of derivative cell populations whose lineages traces to said first cell population, wherein said directed tree includes a plurality of nodes, each node from the plurality of nodes corresponding to one of said derivative cell populations, and directed edges between adjacent nodes representing the linear relationship between respective cell populations;

receiving, at the one or more processors, a genetic profile of or a genetic test result for one of said derivative cell populations;

comparing, at the one or more processors, (1) said genetic profile of said one of said derivative cell populations to the genetic profile of said first cell population based on the directed tree or (2) the genetic test result of said one of said derivative cell populations to the genetic test result of said first cell population, to create a first determination of one or more non-tested derivative cell populations that are intermediate to said first cell population and said one of said derivative cell population along a directed path of said directed tree; and inferring, at the one or more processors, for the one or more non-tested derivative cell populations along a directed path of said directed tree based on said first determination.

2. The method of claim 1, wherein said step of inferring comprises auto-verifying all cell populations in the one or more non-tested derivative cell populations along a directed path of said directed tree of said genetic profile of said one of said derivative cell populations matches a genetic profile of said first cell population.

3. The method of claim 1, wherein said step of inferring comprises auto-verifying all derivative cell populations in the one or more non-tested derivative cell populations along a directed path of said directed tree of said genetic profile of said one of said derivative cell populations matches a reference genetic profile that corresponds to a first cell line.

4. The method of claim 1, further comprising identifying said one of said derivative cell populations as anomalous when said genetic profile of said one of said derivative cell populations does not match the genetic profile of said first cell population.

5. The method of claim 4, wherein said step of inferring includes identifying each cell population in the one or more non-tested derivative cell populations as potentially anomalous based on said identifying of said one of said derivative cell populations as anomalous.

6. The method of claim 5, further comprising identifying any derivative cell populations along an undirected path that does not cross a previously verified cell population of said directed tree from said one of said anomalous cell populations.

7. The method of claim 4, further comprising:
comparing said genetic profile of said one of said derivative cell populations to a second reference genetic profile; and
identifying a contaminant in said one of said derivative cell populations based on said comparing to said second reference genetic profile.

8. The method of claim 1, further comprising:
classifying, at the one or more processors, whether a second cell population is contaminated based on a comparison of the genetic profile for said first cell population and the genetic profile for said one of said derivative cell populations using the digital representation of the directed tree.

9. The method of claim 1, wherein said one of said derivative cell populations is derived from said first cell population by one or more operations from the group including passaging, a freeze-thaw cycle, treatment and modification.

10. The method of claim 1, wherein said second cell population is derived from said first cell population by one or more operations from the group including passaging, a freeze-thaw cycle, treatment and modification.

11. The method of claim 1, wherein said one of said derivative cell populations and said second cell population are of the same cell lineage.

12. The method of claim 11, wherein said one of said derivative cell populations is intermediate between said first cell population and said second cell population in said cell lineage.

13. The method of claim 11, wherein said second cell population is intermediate between said first cell population and said one of said derivative cell populations in said cell lineage.

14. The method of claim 1, wherein:
the first cell population is hosted at a first laboratory; and
said one of said derivative cell populations is hosted at a second laboratory different from the first laboratory;
the method further comprising:
verifying, at the one or more processors, a genetic profile of at least one remaining cell population of said plurality of derivative cell populations based on a comparison of the genetic profile of the first cell population and the genetic profile of said one of said derivative cell populations.

15. The method of claim 14, wherein said comparison of the genetic profiles is performed using data obtained from DNA sequences, including (1) low coverage DNA sequencing, (2) capillary electrophoresis, or (3) genetic stability testing.

16. The method of claim 14, wherein the directed tree describes a cell lineage from said first cell population to said one of said derivative cell populations, the method further comprising:
identifying at least one additional cell population of said plurality of derivative cell populations as being between said first cell population and said one of said derivative cell populations.

17. The method of claim 14, wherein:
the plurality of derivative cell populations are auto-verified when the genetic profile of said one of said derivative cell populations matches said genetic profile of said first cell population,
the genetic profile of the first cell population being received from a device of the first laboratory,
the genetic profile of the one of said derivative cell populations being stored at a device of the second laboratory.

18. The method of claim 17, wherein said comparison of genetic profiles comprises is performed using data obtained from DNA sequences, including (1) low coverage genomic DNA sequencing, (2) capillary electrophoresis, or (3) genetic stability testing.

19. The method of claim 14, wherein the plurality of derivative cell populations are identified as potentially anomalous if the genetic profile of said second one of said derivative cell populations does not match is anomalous compared to said genetic profile of said first cell population.

20. The method of claim 19, wherein said comparison of genetic profiles comprises is performed using data obtained from DNA sequences, including (1) low coverage genomic DNA sequencing, (2) capillary electrophoresis, or (3) genetic stability testing.

* * * * *